United States Patent [19]

Duffett

[11] Patent Number: Plant 6,311

[45] Date of Patent: Sep. 27, 1988

[54] CHRYSANTHEMUM PLANT NAMED DONOS

[75] Inventor: William E. Duffett, Salinas, Calif.

[73] Assignee: Yoder Brothers, Inc., Barberton, Ohio

[21] Appl. No.: 920,163

[22] Filed: Oct. 17, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Donos particularly characterized by its flat capitulum form; anemone capitulum type; yellow-orange ray floret color; good color retention under high light conditions; diameter across face of capitulum of up to 7 cm at maturity when grown as a pinched spray pot mum with diameter of anemone cushion of 3 to 3.5 cm; uniform eight week photoperiodic flowering response to short days; medium plant height when grown as a pinched pot mum, and spreading and prolific branching pattern.

3 Drawing Sheets

The present invention comprises a new and distinct cultivar of Chrysanthemum, botanically known as *Chrysanthemum morifolium*, and referred to by the cultivar name Donos.

Donos, identified as 79U32012, was originated from a cross made by me in a controlled breeding program in Salinas, Calif., in 1979.

The female parent of Donos was the cultivar identified as Russet, disclosed in U.S. Plant Pat. No. 5,107. The male parent of Donos was an unnamed seedling, identified as 79121004.

Donos was discovered and selected as one flowering plant within the progeny of the stated cross by William E. Duffett in November of 1980, in a controlled environment in Salinas, Calif.

The first act of asexual reproduction of Donos was accomplished when vegetative cuttings were taken from the initial selection in March of 1981 in a controlled environment in Salinas, Calif., by technicians working under formulations established and supervised by William E. Duffett.

Horticultural examination of controlled flowerings of successive plantings has shown that the unique combination of characteristics as herein disclosed for Donos are firmly fixed and are retained through successive generations of asexual reproduction.

Donos has not been observed under all possible environmental conditions. The phenotype may vary significantly with variations in environment such as temperature, light intensity, and day length.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Donos, which, in combination, distinguish this Chrysanthemum as a new and distinct cutivar:

1. Flat capitulum form.
2. Anemone capitulum type.
3. Yellow-orange ray floret color.
4. Good color retention under high light conditions.

5. Diameter across face of capitulum up to 7 cm at maturity, with a diameter of anemone cushion of 3 to 3.5 cm when grown as a pinched spray pot mum.

6 Uniform eight week photoperiodic flowering response to short days.

7. Medium plant height, requiring 0 to 7 long days after pinch prior to short days and 1 application of 2500 ppm B-9 SP to attain a flowered plant height of 25 to 35 cm for year-round flowerings when grown as a pinched pot mum.

8. Branching pattern is spreading and prolific.

The accompanying photographic drawings show typical inflorescence and leaf characteristics of Donos, with the colors being as nearly true as possible with illustrations of this type.

Sheet 1 is a color photograph of Donos grown as a pinched spray pot mum.

Sheet 2 is a black and white photograph of three views of the inflorescence of Donos.

Sheet 3 is a black and white photograph showing the upper and under sides of the leaves of Donos at three stages of development (mature, intermediate and immature).

Of the commercial cultivars known to the inventor, the most similar in comparison to Donos is Russet, disclosed in U.S. Plant Pat. No. 5,107. Reference is made to attached Chart A, which compares certain characteristics of Donos to the same characteristics of Russet.

Traits similar to both cultivars are capitulum form and type, branching pattern, plant height and flowering response. Donos differs from Russet by its yellow-orange ray floret color as opposed to the light yellow color of Russet. In addition, the ray floret color of Donos oxidizes very slowly, and Donos has better color retention than Russet, with the ray floret color of Russet oxidizing very rapidly under high light conditions.

In the following description, color references are made to The Royal Horticultural Society Colour Chart. The exact colors for corolla of ray florets and disc florets are not represented in the R.H.S. Color Chart, and the color values given are those closest to the actual color of Donos. The color values were determined from plant material grown as a pinched spray pot mum in Salinas, Calif. on Mar. 14, 1986.

Classification:

*Botanical.*—*Chrysanthemum morifolium,* Ramat., cv. Donos.

*Commercial.*—Anemone spray pot mum.

INFLORESCENCE

A. Capitulum:

*Form.*—Flat.

*Type.*—Anemone.

*Diameter across face.*—Up to 7 cm at maturity, with diameter of anemone cushion up to 3.5 cm.

B. Corolla of ray florets:

*Color (general tonality from a distance of three meters).*—Yellow-orange.

*Color (upper surface).*—11A to 11B, very slightly tinged with 20A.

*Color (under surface).*11A to 11B.

*Shape.*—Flat, oblong.

C. Corolla of disc florets:

*Color (mature).*—15B to 17A.

*Color (immature).*—15B to 17A, tinged with 163A to 163B.

*Shape.*—Elongated, typical anemone.

D. Reproductive organs:

*Androecium.*—Present in disc florets only; scant pollen.

*Gynoecium.*—Present in both ray and disc florets.

PLANT

A. General appearance:

*Height.*—Medium; 25 to 35 cm as a pinched spray pot mum with 0 to 7 long days after pinch prior to short days and 1 application of 2500 ppm B-9 SP.

*Branching pattern.*—Spreading and prolific.

B. Foliage:

*Color (upper surface).*—147A.

*Color (under surface).*—147B.

*Shape.*—Deeply lobed and slightly serrated.

CHART A

COMPARISON OF DONOS AND RUSSET

| CULTIVAR | RAY FLORET COLOR | CAPITULUM FORM & TYPE | BRANCHING PATTERN |
|---|---|---|---|
| DONOS | YELLOW-ORANGE | FLAT ANEMONE | SPREADING |
| RUSSET | LIGHT YELLOW | FLAT ANEMONE | SPREADING |

| CULTIVAR | DIAMETER ACROSS FACE OF CAPITULUM | PLANT HEIGHT |
|---|---|---|
| DONOS | up to 7 cm | MEDIUM |
| RUSSET | up to 9 cm | MEDIUM |

| CULTIVAR | FLOWERING RESPONSE PERIOD | COLOR RETENTION |
|---|---|---|
| DONOS | 8 WEEK | GOOD |
| RUSSET | 8 WEEK | POOR |

COMPARISONS MADE OF PLANTS GROWN AS PINCHED POT MUM IN SALINAS, CALIFORNIA

I claim:

1. A new and distinct Chrysanthemum plant named Donos, as described and illustrated, and particularly characterized as to uniqueness by the combined characteristics of flat capitulum form; anemone capitulum type; yellow-orange ray floret color; good color retention under high light conditions; diameter across face of capitulum of up to 7 cm at maturity when grown as a pinched spray pot mum with a diameter of anemone cushion of 3 to 3.5 cm; uniform eight week photoperiodic flowering response to short days; medium plant height when grown as a pinched pot mum, and by its spreading and prolific branching pattern.

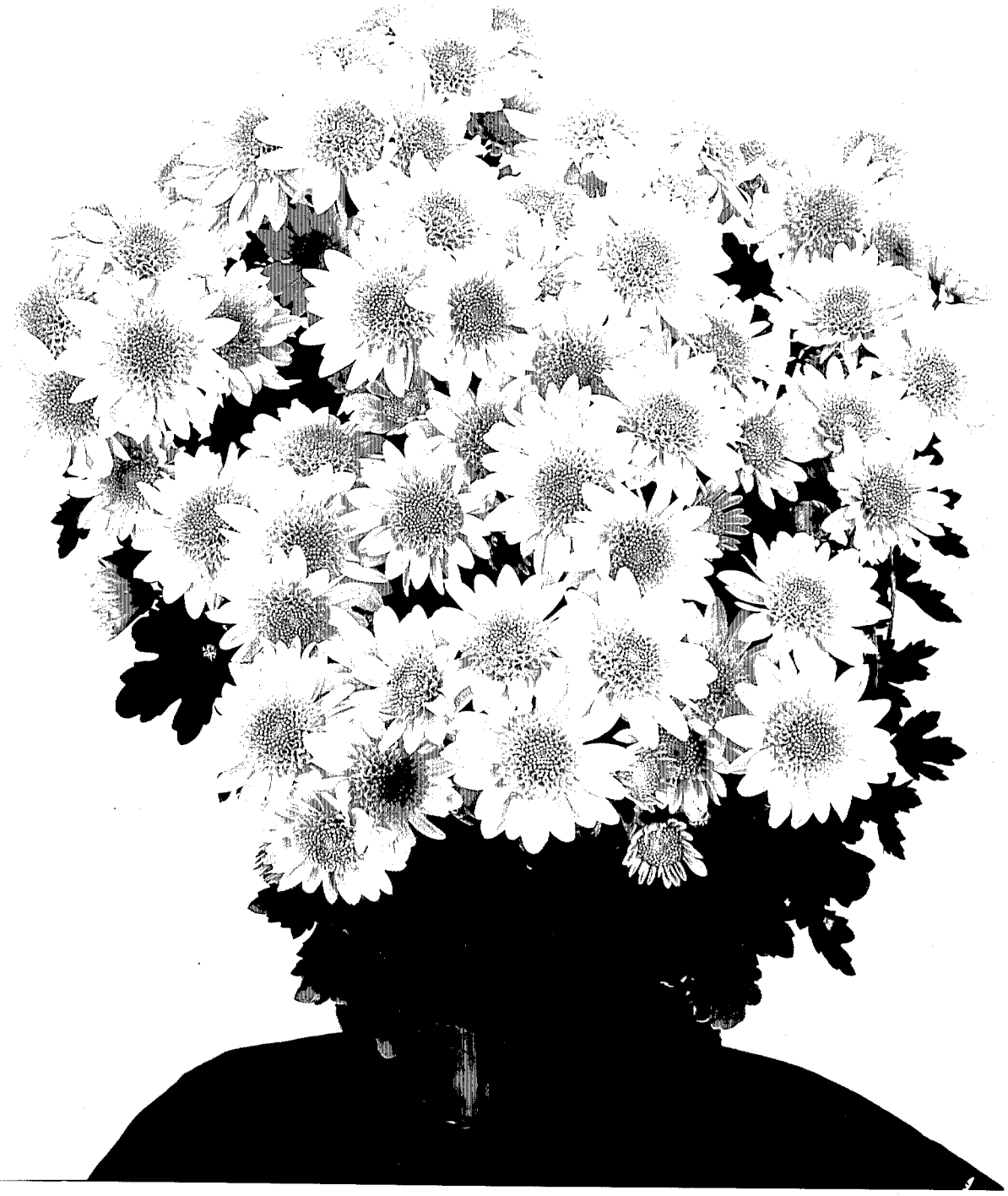

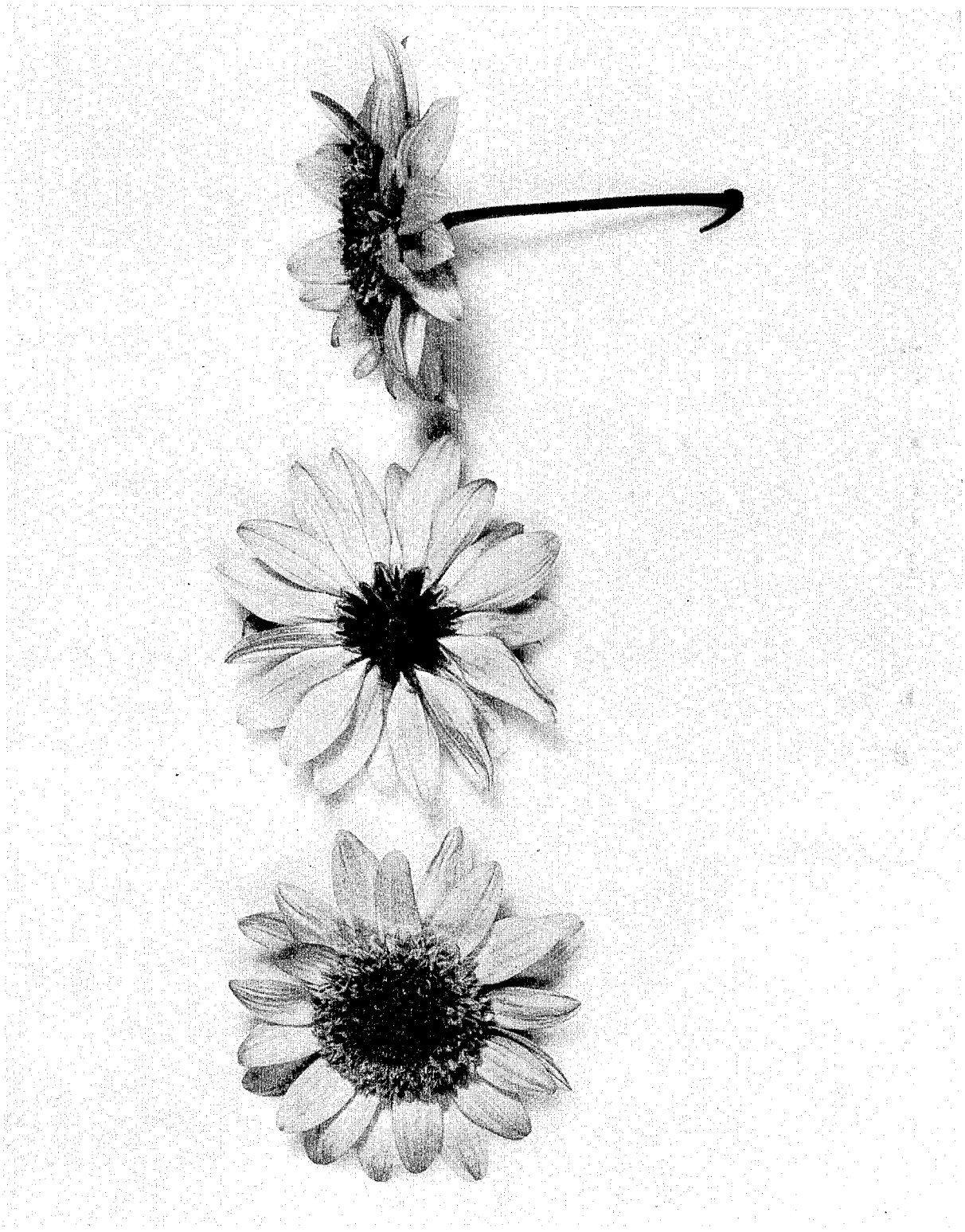

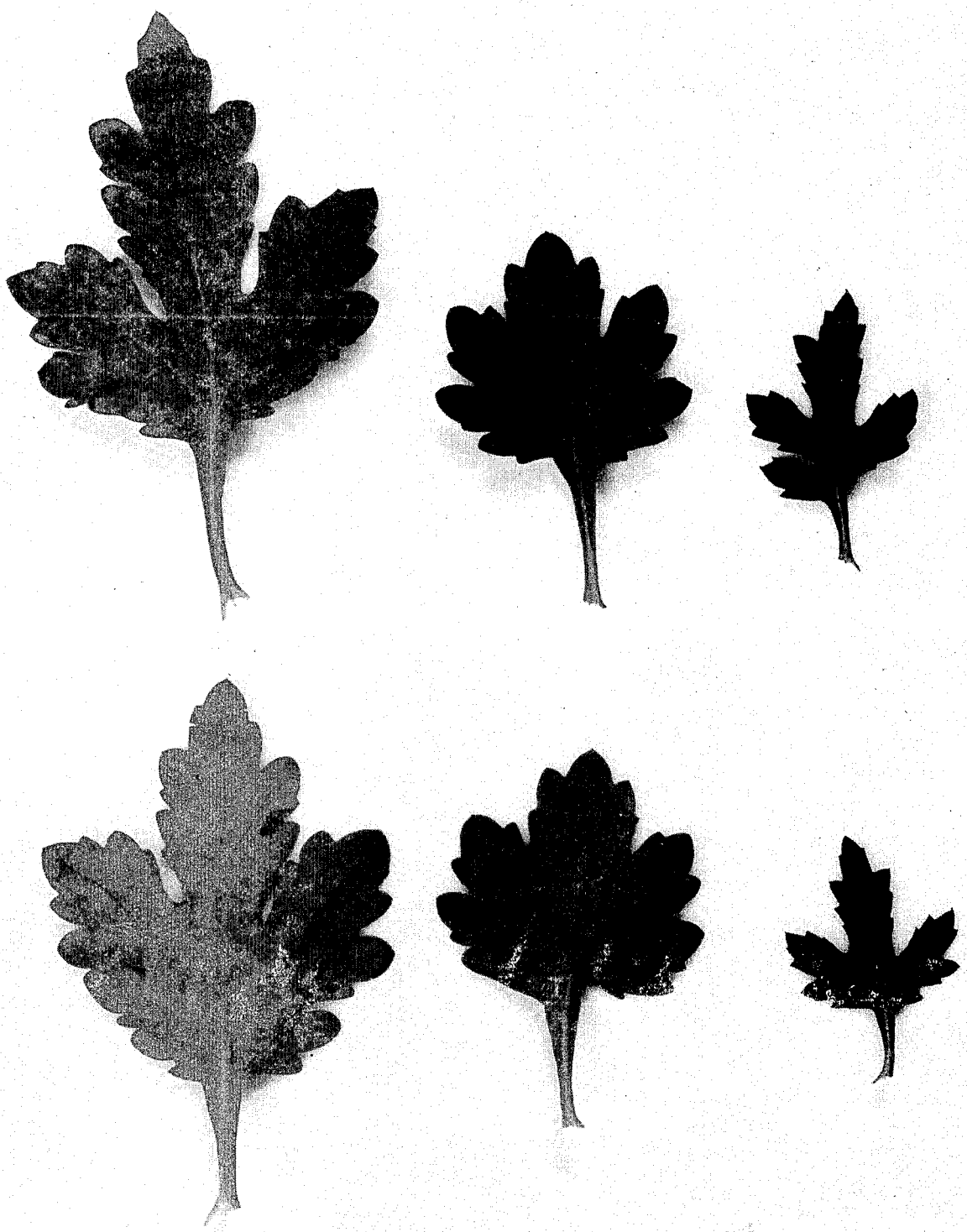

* * * * *